(12) United States Patent
Fellows et al.

(10) Patent No.: US 7,209,783 B2
(45) Date of Patent: Apr. 24, 2007

(54) ABLATION STENT FOR TREATING ATRIAL FIBRILLATION

(75) Inventors: Chris Fellows, Seattle, WA (US); Wade A. Bowe, Temecula, CA (US); David S. Wood, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 698 days.

(21) Appl. No.: 10/123,897

(22) Filed: Apr. 16, 2002

(65) Prior Publication Data

US 2003/0018362 A1 Jan. 23, 2003

Related U.S. Application Data

(60) Provisional application No. 60/298,738, filed on Jun. 15, 2001.

(51) Int. Cl.
*A61F 2/06* (2006.01)
*A61N 1/05* (2006.01)

(52) U.S. Cl. .................. 607/5; 623/1.15; 623/1.11; 607/126; 607/128; 606/41

(58) Field of Classification Search .............. 607/2, 607/5–8; 606/41
See application file for complete search history.

(56) References Cited

U.S. PATENT DOCUMENTS

| 3,692,027 A | 9/1972 | Ellinwood, Jr. .............. 128/260 |
| 4,003,379 A | 1/1977 | Ellinwood, Jr. .............. 128/260 |
| 4,146,029 A | 3/1979 | Ellinwood, Jr. .............. 128/260 |
| 4,281,664 A | 8/1981 | Duggan ....................... 128/696 |
| 4,299,220 A | 11/1981 | Dorman ....................... 128/260 |
| 4,544,371 A | 10/1985 | Dormandy, Jr. et al. ..... 604/891 |
| 4,556,063 A | 12/1985 | Thompson et al. ..... 128/419 PT |
| 4,686,987 A | 8/1987 | Salo et al. ............. 128/419 PG |
| 4,871,351 A | 10/1989 | Feingold ....................... 604/66 |
| 4,897,987 A | 2/1990 | Spaila ......................... 56/16.7 |
| 4,944,299 A | 7/1990 | Silvian .................. 128/419 PG |
| 4,987,897 A | 1/1991 | Funke ................... 128/419 PG |
| 5,040,533 A | 8/1991 | Fearnot ................ 128/419 PG |

(Continued)

FOREIGN PATENT DOCUMENTS

| EP | 0054138 | 6/1982 |
| EP | 1050265 | 11/2000 |
| WO | WO 97/33513 | 9/1997 |

OTHER PUBLICATIONS

Brunner, Friedrich , "Attenuation of Myocardial Ischemia/Reperfusion Injury in Mice with Myocyte-Specific Overexpression of Endothelial Nitric Oxide Synthase", *Cardiovascular Research, 57*, (2003), 55-62.

(Continued)

*Primary Examiner*—Carl Layno
(74) *Attorney, Agent, or Firm*—Schwegman, Lundberg, Woessner & Kluth, P.A.

(57) ABSTRACT

An apparatus and method for treating atrial fibrillation with ablation therapy in which a stent is deployed within a pulmonary vein and tissue surrounding the stent is ablated with radiofrequency energy to stop discharges from ectopic foci in the vein from reaching the left atrium. The deployed stent can then be left in place to prevent stenosis of the vein as well as allowing repeat ablation procedures as needed.

14 Claims, 4 Drawing Sheets

U.S. PATENT DOCUMENTS

| | | | |
|---|---|---|---|
| 5,041,107 A | 8/1991 | Heil, Jr. ................. 604/891.1 |
| 5,042,497 A | 8/1991 | Shapland ................... 600/509 |
| 5,058,581 A | 10/1991 | Silvian ................. 128/419 PG |
| 5,087,243 A | 2/1992 | Avitall ......................... 604/20 |
| 5,127,404 A | 7/1992 | Wyborny et al. ........ 128/419 P |
| 5,190,035 A | 3/1993 | Salo et al. .................. 128/419 |
| 5,220,917 A | 6/1993 | Cammilli et al. ....... 128/419 D |
| 5,269,301 A | 12/1993 | Cohen ........................... 607/6 |
| 5,284,136 A | 2/1994 | Hauck et al. ................. 607/24 |
| 5,305,745 A | 4/1994 | Zacouto ...................... 600/324 |
| 5,342,408 A | 8/1994 | deCoriolis et al. ........... 607/32 |
| 5,353,800 A | 10/1994 | Pohndorf et al. ........... 128/673 |
| 5,368,028 A | 11/1994 | Palti .......................... 128/635 |
| 5,404,877 A | 4/1995 | Nolan et al. ................ 128/671 |
| 5,416,695 A | 5/1995 | Stutman et al. ........ 364/413.02 |
| 5,456,692 A | 10/1995 | Smith, Jr. et al. ............. 607/31 |
| 5,460,605 A | 10/1995 | Tuttle et al. .................. 604/67 |
| 5,496,360 A | 3/1996 | Hoffmann et al. .......... 607/120 |
| 5,499,971 A | 3/1996 | Shapland et al. ............. 604/53 |
| 5,551,953 A | 9/1996 | Lattin et al. .................. 604/20 |
| 5,556,421 A | 9/1996 | Prutchi et al. ................ 607/36 |
| 5,562,713 A | 10/1996 | Silvian ........................ 607/32 |
| 5,579,876 A | 12/1996 | Adrian et al. .......... 188/322.17 |
| 5,586,556 A | 12/1996 | Spivey et al. ............... 600/510 |
| 5,607,418 A | 3/1997 | Arzbaecher .............. 604/891.1 |
| 5,607,463 A | 3/1997 | Schwartz et al. .......... 623/1.44 |
| 5,634,899 A | 6/1997 | Shapland et al. ............. 604/51 |
| 5,662,689 A | 9/1997 | Elsberry et al. ............... 607/5 |
| 5,690,682 A | 11/1997 | Buscemi et al. ............... 607/3 |
| 5,693,075 A | 12/1997 | Plicchi et al. ................. 607/17 |
| 5,720,770 A | 2/1998 | Nappholz et al. ............. 607/30 |
| 5,730,125 A | 3/1998 | Prutchi et al. ............... 128/637 |
| 5,800,498 A | 9/1998 | Obino et al. ................. 607/123 |
| 5,814,089 A | 9/1998 | Stokes et al. .................. 607/32 |
| 5,817,131 A | 10/1998 | Elsberry et al. ............... 607/5 |
| 5,833,603 A | 11/1998 | Kovacs et al. .............. 600/317 |
| 5,836,935 A | 11/1998 | Ashton et al. ........... 604/891.1 |
| 5,893,881 A | 4/1999 | Elsberry et al. ............... 607/5 |
| 5,899,928 A | 5/1999 | Sholder et al. ................ 607/27 |
| 5,925,066 A | 7/1999 | Kroll et al. ..................... 607/3 |
| 5,949,659 A | 9/1999 | Lesche ......................... 363/16 |
| 5,954,761 A | 9/1999 | Macheck et al. ........... 607/126 |
| 5,967,986 A | 10/1999 | Cimochowski et al. ..... 600/454 |
| 5,980,563 A | 11/1999 | Tu et al. ...................... 607/113 |
| 5,980,566 A | 11/1999 | Alt et al. ......................... 623/1 |
| 5,991,668 A | 11/1999 | Leinders et al. ............ 607/125 |
| 6,016,447 A | 1/2000 | Juran et al. .................... 607/27 |
| 6,016,448 A | 1/2000 | Busacker et al. .............. 607/29 |
| 6,024,740 A * | 2/2000 | Lesh et al. ..................... 606/34 |
| 6,115,636 A | 9/2000 | Ryan ............................ 607/60 |
| 6,140,740 A | 10/2000 | Porat et al. .................. 310/322 |
| 6,141,588 A | 10/2000 | Cox et al. ....................... 607/9 |
| 6,154,675 A | 11/2000 | Juran et al. .................... 607/29 |
| 6,168,801 B1 | 1/2001 | Heil, Jr. et al. ............. 424/426 |
| 6,179,789 B1 | 1/2001 | Tu et al. ...................... 600/585 |
| 6,198,394 B1 | 3/2001 | Jacobsen et al. .......... 340/573.1 |
| 6,200,265 B1 | 3/2001 | Walsh et al. ................. 600/300 |
| 6,206,914 B1 | 3/2001 | Soykan et al. .............. 623/1.42 |
| 6,213,942 B1 | 4/2001 | Flach et al. .................. 600/300 |
| 6,231,516 B1 | 5/2001 | Keilman et al. ............. 600/485 |
| 6,237,398 B1 | 5/2001 | Porat et al. .................. 73/54.09 |
| 6,251,109 B1 | 6/2001 | Hassett et al. |
| 6,254,573 B1 | 7/2001 | Haim et al. .................. 604/157 |
| 6,277,078 B1 | 8/2001 | Porat et al. .................. 600/486 |
| 6,298,272 B1 | 10/2001 | Peterfeso et al. ............ 607/120 |
| 6,309,370 B1 | 10/2001 | Haim et al. ................... 604/66 |
| 6,317,615 B1 | 11/2001 | KenKnight et al. ......... 600/372 |
| 6,358,202 B1 | 3/2002 | Arent ........................ 600/300 |
| 6,361,522 B1 | 3/2002 | Scheiner et al. .............. 604/67 |
| 6,361,780 B1 | 3/2002 | Ley et al. ................... 424/400 |
| 6,424,847 B1 | 7/2002 | Mastrototaro et al. ...... 600/316 |
| 6,442,413 B1 | 8/2002 | Silver ........................ 600/345 |
| 6,443,949 B2 | 9/2002 | Altman ........................ 606/41 |
| 6,453,195 B1 | 9/2002 | Thompson ..................... 607/3 |
| 6,459,917 B1 | 10/2002 | Gowda et al. ............... 600/345 |
| 6,501,983 B1 | 12/2002 | Natarajan et al. ........... 600/517 |
| 6,511,477 B2 | 1/2003 | Altman et al. ................. 606/41 |
| 6,514,249 B1 * | 2/2003 | Maguire et al. ............... 606/41 |
| 6,518,245 B1 | 2/2003 | Anderson et al. ............. 514/14 |
| 6,519,488 B2 | 2/2003 | KenKnight et al. ......... 600/372 |
| 6,542,781 B1 | 4/2003 | Koblish et al. ............. 607/172 |
| 6,632,223 B1 * | 10/2003 | Keane .......................... 606/41 |
| 6,645,145 B1 | 11/2003 | Dreschel et al. ............ 600/443 |
| 6,662,045 B2 * | 12/2003 | Zheng et al. ................... 607/5 |
| 6,716,242 B1 | 4/2004 | Altman ...................... 623/1.42 |
| 2001/0000802 A1 | 5/2001 | Soykan et al. .............. 623/1.13 |
| 2002/0026228 A1* | 2/2002 | Schauerte ................... 607/122 |
| 2003/0004403 A1 | 1/2003 | Drinan et al. ............... 600/301 |
| 2003/0069606 A1 | 4/2003 | Girouard et al. ............... 607/3 |
| 2003/0158584 A1 | 8/2003 | Cates et al. .................... 607/2 |

OTHER PUBLICATIONS

Burns, Brent E., "Fabrication Technology for a Chronic In-Vivo Pressure Sensor", *1984 International Electron Devices Meeting Technical Digest*, (1984),210-212.

Carr, William N., "Integrated Pressure Sensor With Remote Power Source and Remote Readout", *The 8th International Conference on Solid-State Sensors and Actuators and Eurosensors IX, Digest of Technical Papers*, Stockholm, Sweden, (Jun. 25-29, 1995),624-627.

Chau, Hin-Leung , "An Ultraminiature Solid-State Pressure Sensor for a Cardiovascular Catheter", *IEEE Transactions on Electron Devices*, (Dec., 1988),2355-2362.

Flögel, Ulrich, "Myoglobin: A Scavenger of Bioactive NO", *PNAS, 98(2)*, (Jan. 16, 2001),735-740.

Gewaltig, Michael T., "Vasoprotection by Nitric Oxide: Mechanisms and Therapeutic Potential", *Cardiovascular Research, 55*, (Feb. 14, 2002),250-260.

Li, Qianhong , "Gene Therapy With Inducible Nitric Oxide Synthase Protects Against Myocardial Infarction via a Cyclooxygenase-2-Dependent Mechanism", *Circulation Research, 92*, (2003),741-748.

Paolocci, Nazareno , "Positive Inotropic and Lusitropic Effects of HNO/NO- in Failing Hearts: Independence From Beta-Adrenergic Signaling", *Proceedings of the National Academy of Sciences USA, 100(9)*, (Apr. 29, 2003),4978-80.

Pastore, Joseph M., "Method and Apparatus for Modulating Cellular Metabolism During Post-Ischemia or Heart Failure", *U.S. Appl. No. 10/645,823, filed Aug. 21, 2003*, 46 pages.

Salloum, Fadi , "Sildenafil Induces Delayed Preconditioning Through Inducible Nitric Oxide Synthase-Dependent Pathway in Mouse Heart", *Circulation Research, 92*, (Apr. 4, 2003),595-597.

Spiegel, Egbert , "A CMOS Sensor and Signal Conversion Chip for Monitoring Arterial Blood Pressure and Temperature", *IEEE International Solid-State Circuits Conference,*, (Feb. 20, 1992),126-127.

Wunderlich, Carsten , "Acute Inhibition of Myoglobin Impairs Contractility and Energy State of iNOS-Overexpressing Hearts", *Circulation Research, 92*, (2003),1352-1358.

Ziaie, Babak , "A Single-Channel Implantable Microstimulator for Functional Neuromuscular Stimulation", *IEEE Transactions on Biomedical Engineering, 44*, (Oct., 1997),909-920.

Hunter, W. L., et al., "Local delivery of chemotherapy: a supplement to existing cancer treatments A case for surgical pastes and coated stents", *Advanced Drug Delivery Reviews, 26*, (1997), 199-207.

Tsai, C. F., et al., "Initiation of atrial fibrillation by ectopic beats originating from the superior vena cava: electrophysiological characteristics and results of radiofrequency ablation", *Circulation [NLM-Medicine], 102, iss. 1*, (Jul. 4, 2000), 67-74.

* cited by examiner

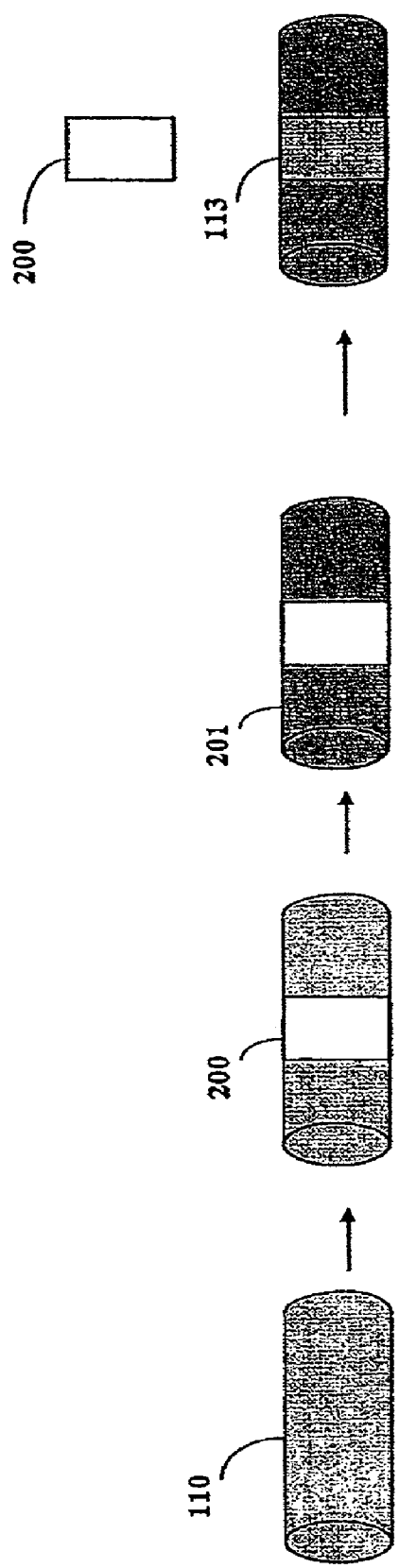

ABLATION STENT FOR TREATING ATRIAL FIBRILLATION

CROSS-REFERENCE TO RELATED APPLICATION(S)

This application claims the benefit of U.S. Provisional Application No. 60/298,738, filed on Jun. 15, 2001, under 35 U.S.C. 119(e).

FIELD OF THE INVENTION

This invention pertains to methods for treating atrial tachyarrhythmias such as atrial fibrillation. In particular, the invention relates to an apparatus and method for treating atrial fibrillation by ablation therapy.

BACKGROUND

Fibrillation refers to a condition in which muscle fibrils enter a state of extremely rapid, small-scale contractions that do not coordinate to effect contraction of the muscle as a whole. When this occurs in the left ventricle, the heart chamber responsible for pumping blood into the arterial vasculature, it is serious and rapidly fatal. When it occurs in the musculature of the atria, it is less immediately serious and not necessarily fatal. It is still important to treat atrial fibrillation, however, for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy, in-hospital cardioversion, and implantable cardioverter/defibrillators are acceptable treatment modalities for atrial fibrillation, a curative approach such as ablation therapy offers a number of advantages to certain patients, including convenience and greater efficacy.

Electrical ablation therapy treats cardiac arrhythmias by destroying myocardial tissue involved in the initiation or maintenance of the tachyarrhythmia. Ablation is most often accomplished by delivering radiofrequency electrical energy through a catheter electrode that has been placed next to the tissue to be destroyed. One way that the technique has been employed in order to treat atrial fibrillation is to identify ectopic sites or reentrant pathways electrophysiologically and then eliminate them by radiofrequency catheter ablation. Recent evidence has shown that the great majority of paroxysms of atrial fibrillation are initiated by trains of rapid discharges originating from the pulmonary veins. Accordingly, catheter techniques have been developed for ablating these sites with radiofrequency energy applied from within the pulmonary veins, but electrophysiological mapping of such sites is difficult. Alternatively, another technique involves the production of a circumferential ablation lesion within a pulmonary vein in order to block the conduction pathway from the vein to the left atrium. An effective circumferential lesion must be completely continuous, however, and this means that the ablation device must be precisely located within the vein or ostium, which may be difficult to accomplish. Furthermore, a common complication of this procedure is pulmonary venous stenosis resulting from scarring within the pulmonary vein which has variable clinical consequences.

SUMMARY OF THE INVENTION

An objective of the present invention is to provide an improved apparatus and method for pulmonary vein ablation in order to treat atrial fibrillation. In accordance with the invention, a stent catheter having a stent mounted thereon is introduced into the left atrium of a patient. The stent is deployed by expansion of the stent within a pulmonary vein or ostium of the vein. The stent expansion may be performed with a balloon at the distal end of the stent catheter or by a self-expanding stent. Tissue surrounding the deployed stent is then ablated to stop discharges from ectopic foci in the vein from reaching the left atrium. After the ablation, the stent is left in place in order to prevent stenosis of the vein.

In order to produce the ablation, radiofrequency energy is transmitted into the surrounding tissue by means of a catheter making contact with the stent which then causes heating of the surrounding tissue. The stent may have electrodes for transmitting current to the surrounding tissue or the stent itself may be used as an electrode. The ablation lesions in the tissue surrounding the stent may be selectively produced so as to destroy one or more ectopic foci, or a circumferential lesion may be produced that interrupts a conduction pathway between the vein and the left atrium.

BRIEF DESCRIPTION OF THE DRAWINGS

FIGS. 3A–3D depict the steps in one method for forming an electrode on the surface of a stent.

DETAILED DESCRIPTION OF THE INVENTION

As noted above, it has been found that the ectopic foci responsible for most episodes of atrial fibrillation are found in the pulmonary veins. The pulmonary veins empty into the left atrium, and a myocardial muscle sleeve extends over the proximal segment of the veins. The myocytes in these pulmonary vein sleeves, unlike ordinary atrial myocytes, exhibit spontaneous activity and can thus constitute ectopic sites responsible for initiating and maintaining atrial fibrillation. In order to block the discharges from these myocytes with ablation therapy, either the myocytes themselves are destroyed or an ablation lesion is made that destroys excitable tissue in the pathway leading from the myocytes to the left atrium.

Figure 1A:
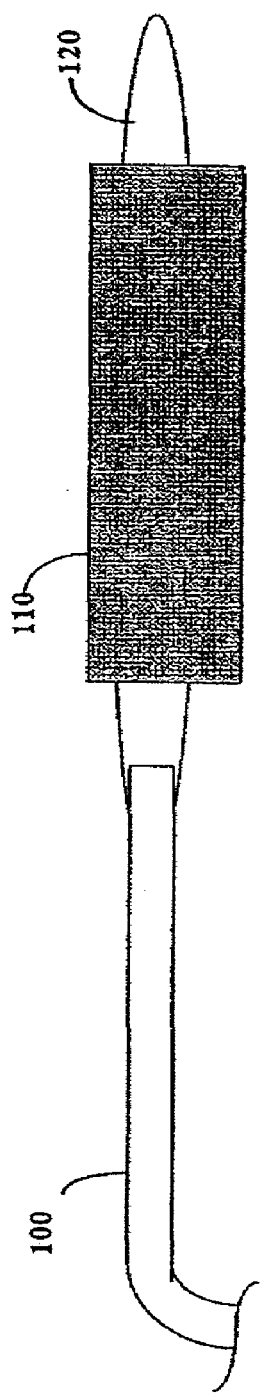
FIG. 1A depicts a stent catheter with a stent mounted at one end.

Shown in FIG. 1A is a depiction of a stent catheter 100 having a balloon 120 at its distal end. Fitted around the balloon 120 is a vascular stent 110, which is a tubular structure made of metal or synthetic material capable of being deployed in a pulmonary vein similar to the way arterial stents are deployed in peripheral or coronary arteries. Pressurized fluid applied to the proximal end of the catheter passes through a lumen within the catheter and inflates the balloon 120. Inflating the balloon 120 expands the stent 110 against the walls of a blood vessel and thereby deploys the stent in a fixed position within the vessel. In an alternate embodiment, the stent may be designed to be self-expanding such as by mechanical means or by being constructed of a shape-memory alloy such as nitinol.

The stent catheter 100 with the stent 110 fixed thereon may be positioned in a pulmonary vein using an over the wire catheterization technique in which a radio-opaque catheter, or guidewire over which the catheter slides, is passed into a patient's vascular system under fluoroscopic guidance. Vascular access is obtained by puncturing a vessel and seating a hemostatic valve within the puncture wound. The stent catheter is then passed into the patient's vascular system through the valve. In one approach, the catheter is introduced into a peripheral vein and then advanced through the vena cava and into the right atrium. From there, the catheter is positioned against the fossa ovalis in the atrial septum, and a needle or trochar is advanced distally through a lumen of the stent catheter and out the distal end to puncture the fossa ovalis. The catheter is then passed through the atrial septum to reach the left atrium and gain access to the pulmonary veins. In another approach, the catheter is advanced into the left atrium from the arterial system by accessing a peripheral artery and advancing the catheter into the aorta, around the aortic arch, into the left ventricle, and then into the left atrium through the mitral valve. With either approach, after reaching the left atrium, the distal end of the stent catheter 100 is advanced into a selected pulmonary vein to position the stent 110 within either the vein or the ostium of the vein where the conduction block is to be formed. Alternatively, the stent deployment could be done during open-heart surgery or a transthoracic surgical procedure. In that case, rather than a catheter, a plunger-type instrument could be used to deploy the stent and apply energy thereto to produce the ablation lesion. Saline infusion for cooling could also be applied through the plunger type instrument.

The stent 110 is deployed by expanding the stent within the vein by, for example, inflating balloon 120 over which the stent 110 is fitted. Tissue surrounding the deployed stent is then ablated so as to stop discharges from ectopic foci in the vein from reaching the left atrium. The ablation lesions in the tissue surrounding the stent may be selectively produced so as to destroy one or more ectopic foci, or a circumferential lesion may be produced that interrupts a conduction pathway between the vein and the left atrium. After the ablation lesion has been produced, the stent is left in place in order to prevent stenosis of the vein as a result of fibrosis and scarring.

Figure 1B:
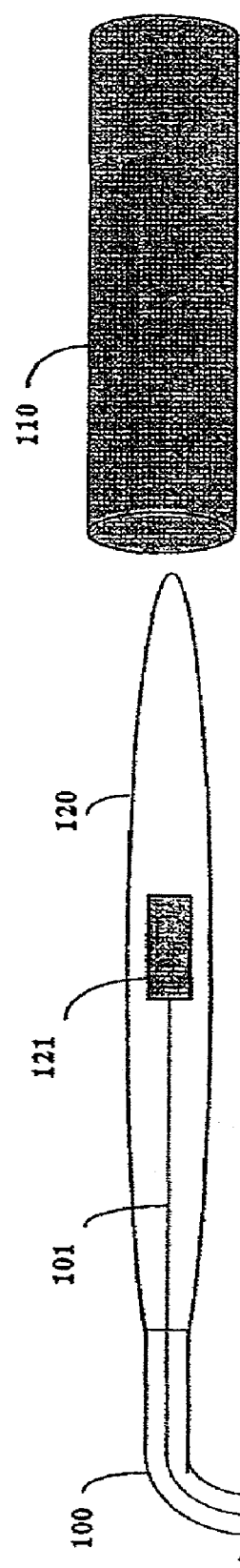
FIG. 1B shows a balloon catheter with an electrode for delivering energy to a deployed stent.

In order to produce the ablation lesion, radiofrequency energy is applied to the stent which causes thermal heating of the surrounding tissue. The result is either a circumferential conduction block around the vein which isolates myocytes in the vein distal to the lesion or localized destruction of ectopic foci. Such energy can be applied from the stent catheter or from a separately introduced ablation catheter which contacts the stent and transmits electrical energy thereto. FIG. 1B shows an embodiment of a stent catheter 100 in which an electrode 121 is mounted on the balloon 120. The electrode 121 is connected internal to the balloon to a conductor 101 that extends through the lumen of the catheter so that electrical energy can be applied to the electrode. With either a catheter such as that shown in FIG. 1B or a separate ablation catheter, radiofrequency energy is transmitted from the catheter to the stent which either acts as an electrode or has separate ablation electrodes mounted thereon as described below.

Figure 2A:
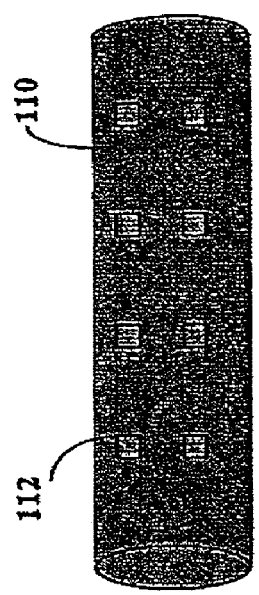
FIG. 2A shows one embodiment of a stent with annular electrodes.
Figure 2B:
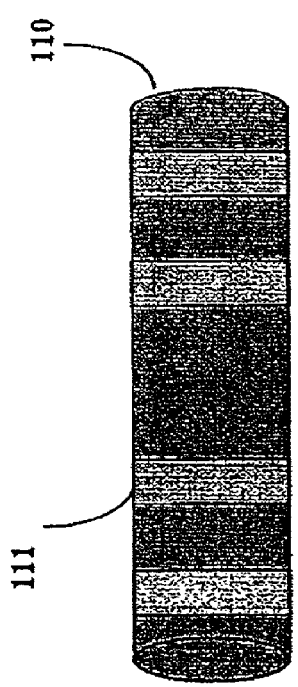
FIG. 2B shows an embodiment of a stent with a plurality of patch electrodes.

The stent itself may be used as an electrode or may have separate electrodes for transmitting current to the surrounding tissue. In the former case, the stent may be made of any electrically conductive material such as platinum, silver, gold, stainless steel, nitinol, or titanium. FIG. 2A shows an exemplary stent design in which the stent 110 has one or more annular electrodes 111 mounted thereon which effect a cirumferential burn when radiofrequency energy is applied to the electrodes. Preferably, the annular electrodes are constructed so as to produce a circumferentially continuous lesion when electrical energy is applied. FIG. 2B shows another embodiment in which the stent 110 has one or more patch electrodes 112 placed at selected locations on the surface of the stent. Such patch electrodes are electrically conductive areas on the stent surface which may be of any desired shape.

Separate electrodes on the stent may be of the same material or a separate material which may be formed on the stent by, for example, sputter coating or vapor deposition. FIGS. 3A through 3D show one method for making an annular electrode on a stent. FIG. 3A shows a stent 110 made of electrically conductive material. An annular mask 200 is then applied to the stent 110 at the location where an electrode is desired as shown in FIG. 3B. Next, a non-conductive dielectric coating 201 is applied to the entire stent as shown in FIG. 3C. FIG. 3D shows the resulting stent with an electrically conductive annular electrode 113 after the mask is removed.

Figure 4:
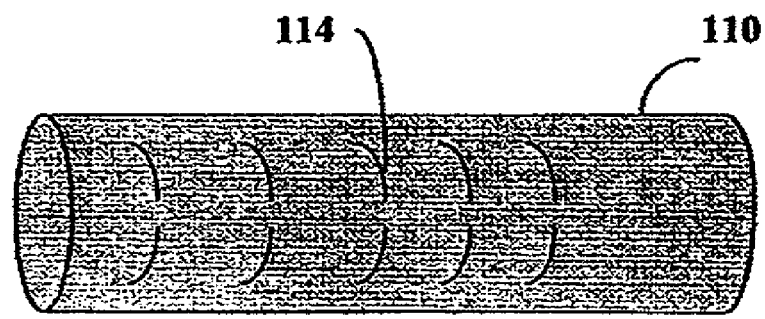
FIG. 4 shows another embodiment of a stent with structures for preventing dislodgement after the stent is deployed.

In order to reduce the risk of thrombus formation, a coating of heparin or other anti-coagulant can be applied to the stent before deployment. In addition, mechanical anchoring devices may be incorporated into the stent in order to prevent dislodgement after the stent is deployed. FIG. 4 illustrates one example of such a stent in which a plurality of hooks 114 are mounted on a stent 110. The hooks 114 are oriented so as to allow the stent to be pushed retrogradely through a pulmonary vein without resistance but prevent it from being pushed out in the other direction by blood flow. Other anchoring devices mounted on the stent, such as tines, spikes, or barbs, may similarly be employed to fix the stent in place after deployment.

Figure 5:
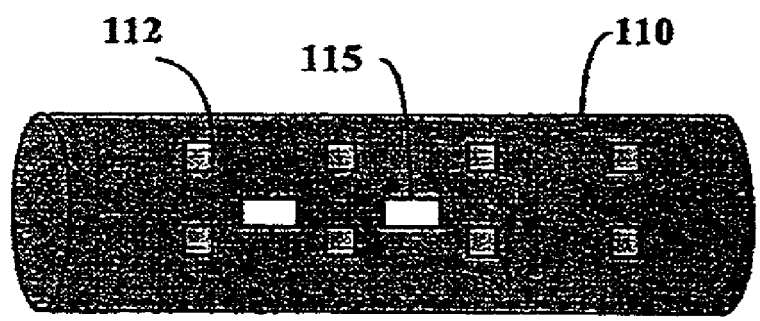
FIG. 5 shows a stent with temperature sensing elements.

During the ablation procedure, it may be useful to monitor the temperature of the tissue as it is heated by the ablation electrodes. Accordingly, FIG. 5 illustrates a modified ablation stent 110 with ablation electrodes 112 and which also has one or more temperature sensors 115 mounted thereon. The temperature sensors (e.g., thermocouples or resistive temperature devices) are connected via a conductor running through the catheter to monitoring equipment at the proximal end of the catheter in order to provide feedback to an operator as current is supplied to the ablation electrodes.

As described above, using a deployed vascular stent as a vehicle for delivering ablation energy to a selected location greatly facilitates the ablation procedure and produces more consistent results. In the event a first ablation procedure is not satisfactory, however, having the stent already deployed also allows any repeat ablation procedures to be more easily performed.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for treating atrial fibrillation, comprising:
    introducing a stent into the left atrium of a patient, wherein the stent is introduced by a stent catheter having a stent mounted at its distal end;
    deploying the stent into a pulmonary vein by inflating a balloon at the distal end of the stent catheter to expand the stent within a pulmonary vein, applying radiofrequency energy to the deployed stent in order to ablate surrounding tissue and stop discharges from ectopic foci in the vein from reaching the left atrium, leaving the stent in place in order to prevent stenosis of the vein; and, transmitting the radiofrequency energy to the stent by an electrode mounted on the surface of the balloon.

2. The method of claim 1 further comprising transmitting the radiofrequency energy into the surrounding tissue by means of a catheter making contact with the stent.

3. The method of claim 1 wherein the stent acts as an electrode when radiofrequency energy is applied thereto so that tissue surrounding the stent is ablated and forms a circumferential lesion that interrupts a conduction pathway between the vein and the left atrium.

4. The method of claim 1 wherein radiofrequency energy is applied to electrodes mounted on the stent to thereby ablate tissue in contact with the electrodes.

5. The method of claim 1 wherein the stent has one or more anchoring devices mounted thereon that serve to prevent dislodgment after the stent is deployed in a pulmonary vein.

6. The method of claim 1 further comprising performing one or more additional ablation procedures after the stent is deployed by applying radiofrequency energy to the deployed stent if a first ablation procedure did not produce satisfactory results.

7. The method of claim 1 further comprising advancing the stent catheter transvenously into the left atrium through the atrial septum.

8. An apparatus for treating atrial fibrillation, comprising:
a stent catheter having a stent mounted thereon for deployment in a pulmonary vein, the catheter including a balloon at its distal end for expanding the stent within a pulmonary vein and,
an electrode located on the surface of the balloon for making contact with the deployed stent and for transmitting radiofrequency energy thereto in order to ablate surrounding tissue and stop discharges from ectopic foci in the vein from reaching the left atrium.

9. The apparatus of claim 8 further comprising one or more electrodes mounted on the stent for contacting surrounding tissue and producing an ablation lesion when energy is applied thereto.

10. The apparatus of claim 8 wherein the stent electrode is an annular electrode.

11. The apparatus of claim 8 wherein the stent electrode is a patch electrode.

12. The apparatus of claim 8 wherein the stent is constructed of an electrically conductive material and further wherein a dielectric coating is applied to the outer surface of the stent leaving a selected area exposed to serve as an electrode.

13. The apparatus of claim 8 further comprising one or more anchoring devices mounted on the surface of the stent to prevent dislodgement after the stent is deployed.

14. An apparatus for treating atrial fibrillation, comprising:
a stent catheter means having a stent mounted thereon for deployment in a pulmonary vein, the catheter including a balloon at its distal end for expanding the stent within a pulmonary vein, wherein the stent is coated with an anti-coagulant to prevent thrombus formation;
one or more anchoring devices mounted on the surface of the stent to prevent dislodgment after the stent is deployed; and,
an electrode located on the surface of the balloon for transmitting radiofrequency energy to the deployed stent in order to ablate surrounding tissue and stop discharges from ectopic foci in the vein from reaching the left atrium.

* * * * *

UNITED STATES PATENT AND TRADEMARK OFFICE
CERTIFICATE OF CORRECTION

| | |
|---|---|
| PATENT NO. | : 7,209,783 B2 |
| APPLICATION NO. | : 10/123897 |
| DATED | : April 24, 2007 |
| INVENTOR(S) | : Fellows et al. |

Page 1 of 1

It is certified that error appears in the above-identified patent and that said Letters Patent is hereby corrected as shown below:

On the title page, in field (56), under "U.S. Patent Documents" in column 2, line 8, delete "Spaila" and insert -- Spalla --, therefor.

Signed and Sealed this

Tenth Day of July, 2007

JON W. DUDAS
*Director of the United States Patent and Trademark Office*